(12) United States Patent
Filippini et al.

(10) Patent No.: US 6,448,228 B1
(45) Date of Patent: Sep. 10, 2002

(54) DIPEPTIDE COMPOUNDS HAVING A HIGH FUNGICIDAL ACTIVITY AND THEIR AGRONOMIC USE

(75) Inventors: Lucio Filippini, San Donato Milanese; Marilena Gusmeroli, Monza; Silvia Mormile, Novara; Laura Colombo, Lodi; Luigi Mirenna, Milan, all of (IT)

(73) Assignee: Isagro Ricerca S.r.l., Milan (IT)

( * ) Notice: Subject to any disclaimer, the term of this patent is extended or adjusted under 35 U.S.C. 154(b) by 0 days.

(21) Appl. No.: 09/450,950

(22) Filed: Nov. 29, 1999

(30) Foreign Application Priority Data

Nov. 30, 1998 (IT) .......................... MI98A2583

(51) Int. Cl.[7] .................................. C07K 5/06
(52) U.S. Cl. .................... 514/19; 526/575; 562/567
(58) Field of Search ................ 514/19; 526/575; 562/567

(56) References Cited

U.S. PATENT DOCUMENTS 5,811,424 A 9/1998 Shibata et al. ............ 514/237.5

FOREIGN PATENT DOCUMENTS

| EP | 0 652 229 | 5/1995 |
|----|-----------|--------|
| EP | 0 718 280 | 6/1996 |

*Primary Examiner*—Christopher S. F. Low
(74) *Attorney, Agent, or Firm*—Oblon, Spivak, McClelland, Maier & Neustadt, P.C.

(57) ABSTRACT

The invention relates to dipeptide compounds having formula (I):

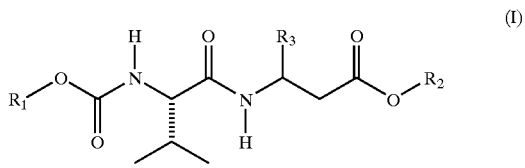

The compounds having formula (I) have a high antifungal activity and are used for the control of phytopathogens in the agronomic field.

47 Claims, No Drawings

DIPEPTIDE COMPOUNDS HAVING A HIGH FUNGICIDAL ACTIVITY AND THEIR AGRONOMIC USE

FIELD OF THE INVENTION

The present relates to new dipeptide compounds capable of controlling phytopathogens which cause considerable economic damage to agricultural crops.

More specifically, the present invention relates to new dipeptide compounds capable of effectively controlling phytopathogens of crops of great economic interest, such as, for example, vines, potatoes and tobacco, as well as their agronomic use, alone or mixed with one or more active principles with a fungicidal activity, and the process for their preparation.

DESCRIPTION OF THE RELATED ART

The patent application EP 652 229 A2 discloses suitably functionalized oligopeptide compounds having a high fungicidal activity consisting of one or two aliphatic amino acids, such as valine, leucine and isoleucine, conjugated to one or two aromatic amino acids, such as phenyl-glycine, phenylalanine and β-phenylalanine (or 3-amino-3-phenylpropanoic acid), whose free amine and carboxyl functions can also be suitably functionalized.

Patent application EP 718 280 A2 again describes compounds based on 3-amino-3-arylpropanoic acids suitably substituted. Among the compounds based on 3-amino-3-arylpropanoic acids claimed, there are also dipeptide compounds obtained by means of bonds between the amine group of said 3-amino-3-arylpropanoic acids and the carboxyl group of an amino acid, such as valine appropriately functionalized on its amine function.

Said patent applications EP 652 229 A2 and EP 718 280 A2, among the numerous examples which illustrate the invention, describe dipeptlde compounds, whose basic skeleton consists of L-valine conjugated by means of its carboxyl group with an aromatic β-amino acid (3-amino-3-arylpropanoic acid) and whose structures can be defined by a single general formula (Ia):

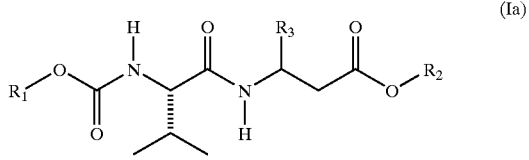

wherein:
R$_1$ represents a linear or branched C$_1$–C$_8$ alkyl group, or a phenyl group;
R$_2$ represents a linear or branched C$_1$–C$_8$ alkyl group;
R$_3$ can be a phenyl group optionally substituted.

On the basis of what is described in the above patent applications, these dipeptide compounds are particularly effective in the control of Oomycetes.

The products specified which can be defined by this general formula are generally characterized by the functionalization of the amine residue with a carboxy-tertbutyl group (R$_1$ therefore means tert-butyl) or by the esterification of the carboxyl residue with an alkyl group, and the R$_2$ group therefore has the meaning of a methyl, ethyl and isopropyl group, in the presence of an R$_3$ phenyl group.

The compounds having general formula Ia also allow synergic fungicidal mixtures to be obtained with the levorotatory isomer of methyl (N-phenylacetyl-N-2,6-xylyl) alaninate (Benalaxyl), as described in the patent WO 98 26654 A2.

BRIEF SUMMARY OF THE INVENTION

The Applicant has now found that new dipeptide compounds having formula (I), which have never been described before, have a higher fungicidal activity than those of the dipeptide compounds specified in the known art.

DETAILED DESCRIPTION OF THE INVENTION

The present invention therefore relates to dipeptide compounds having formula (I):

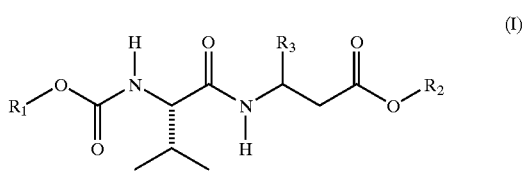

wherein:
R$_1$ represents an isopropyl or phenyl group;
R$_2$ represents a methyl group;
R$_3$ can be a phenyl group substituted in position 4 with an R$_4$ group; or it can represent a 2-benzothiazole group, optionally substituted with an R$_5$ group;
R$_4$ and R$_5$ can be a fluorine or chlorine atom; a methyl or ethyl group; or a methoxyl group; or they can represent a cyano group.

The configuration of the atom of the valine residue present in all compounds having formula (I) is S, according to the Cahn, Ingold and Prelog convention.

The absolute configuration of the chiral atom of aromatic β-amino acid incorporated in the dipeptide compound may, on the contrary, be either S or R.

The compounds of the present invention, considering jointly the asymmetrical centres present in the molecule, may be in diastereoisomeric forms S—S or S—R, wherein the first letter refers to the chiral centre of valine whereas the second letter describes the chiral centre of aromatic β-amino acid, or they can be present as a diastereoisomeric mixture in which the two forms are in any molar ratio.

The Applicant has found that compounds in which the absolute configuration of the chiral atom of aromatic β-amino acid incorporated in the dipeptide compound is R, have a greater fungicidal activity.

A particular aspect of the present invention therefore relates to dipeptide compounds having formula (I) wherein the absolute configuration of the chiral atom of the β-amino acid residue is R, as represented by general formula (II)

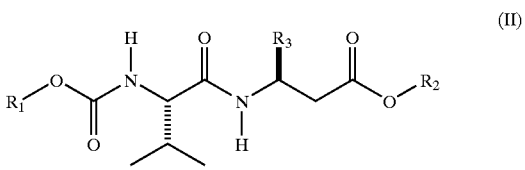

wherein:
R$_1$, R$_2$, R$_3$ have the meaning defined above (formula I).
The compounds of the present invention can be conveniently used in agriculture as a diastereoisomeric mixture in which the two forms can be present in any molar ratio.

According to present conventions, a compound having formula (I) with an epimeric form S—RS contains these diastereoisomeric forms S—S and S—R in an equimolecular ratio.

Owing to the higher activity of compounds in which the absolute configuration of the chiral atom of aromatic β-amino acid is R, the compounds having formula (I) are preferably used as a diastereoisomeric mixture in which the diastereoisomeric form S—R is greater than 80%.

Even more preferable are diastereoisomeric mixtures in which the diastereoisomeric form S—R is present in greater quantities, such as, for example, diastereoisomeric mixtures containing the form S—R in quantities exceeding 90%, 95% or 98%.

The use of compounds having formula (I) in the sole dlastereoisomeric form S—R, is the most preferable.

The compounds having formula (I) can be used alone or optionally associated with at least one other compound having a fungicidal activity.

The present invention therefore relates to fungicidal compositions comprising:
a) a dipeptide compound having formula (I) as a diastereoisomeric mixture in which the two forms can be present in any molar ratio, or as a sole diasatereoisomeric form S—R;
b) one or more fungicides selected from:
(1) Cymoxanil corresponding to 1-(2-cyano-2-methoxyimino-acetyl)-3-ethylurea;
(2) Fosetyl-Al corresponding to the aluminum salt of ethyl hydrogen phosphonate;
(3) Potassium phosphonate;
(4) Benalaxyl corresponding to methyl N-(phenyl-acetyl)-N-2,6-xylyl-RS-alaninate;
(5) Methyl N-(phenylacetyl)-N-2,6-xylyl-R-alaninate;
(6) Metalaxyl corresponding to methyl N-(2-methoxyacetyl)-N-2,6-xylyl-RS-alaninate;
(7) Mefenoxam corresponding to methyl N-(2-methoxyacetyl-N-2,6-xylyl-R-alaninate;
(8) Oxadixyl corresponding to 2-methoxy-N-(2-oxo-1,3-oxazolidin-3-yl)acet-2',6'-xylidinide;
(9) Ofurace corresponding to DL-3-[N-chloroacetyl-N-(2,6-xylyl)-amino]-γ-butyrolactone;
(10) Iprovalicarb corresponding to O-(1-methylethyl)-N-[2-methyl-1-[[[1-(4-methylphenyl)ethyl]-amino]carbonyl]propyl]carbamate;
(11) Azoxystrobin corresponding to methyl (E)-2-[2-[6-(2-cyanophenoxy)-pyrimidin-4-yloxy]phenyl]-3-methoxyacrylate;
(12) Kresoxym-methyl corresponding to methyl (E)-methoxyimino-α-[o-tolyloxy)-o-tolyl]acetate;
(13) Metominofen corresponding to the experimental abbreviation SSF-126 and corresponding to N-methyl-(E)-methoxyimino-(2-phenoxyphenyl)acetamide;
(14) Acylbenzolar corresponding to methylbenzothiadiazole-7-thiocarboxylate;
(15) Famoxadone corresponding to 5-methyl-5-(4-phenoxyphenyl)-3-(phenylamino)oxazolidin-2,4-dione;
(16) Fenamidone corresponding to 4-methyl-4-phenyl-1-(phenylamino)-2-methylthioimidazolidin-5-one;
(17) IKF916 corresponding to 2-cyano-4-chloro-5-(4-methylphenyl)-1-(N,N-dimethylaminosulfamoyl)-imidazole;
(18) Fluazinam corresponding to 3-chloro-N-(3-chloro-5-trlfluoromethyl-2-pyridyl)-α,α,α-tri-fluoro-2,6-dinitro-p-toluidine;
(19) Dimethomorph corresponding to (E,Z)-4-[3-(4-chlorophenyl)-3-(3,4-dimethoxyphenyl)acryloyl]morpholine;
(20) Flumetover corresponding to N,N-diethylamide of 4-trifluoromethyl-6-(3,4-dimethoxyphenyl)benzoic acid;
(21) Chlorothalonil corresponding to 1,3-dicyano-2,4,5,6-tetrachlorobenzene;
(22) Thiram corresponding to bis-(dimethylthiocarbamoyl)disulfide (polymer);
(23) Propineb corresponding to the zinc salt of propylenebis(dithiocarbamate)(polymer);
(24) Mancozeb corresponding to the manganese and zinc salt of ethylenebis(dithiocarbamate) (polymer);
(25) Maneb corresponding to the manganese salt of ethylenebis(dithiocarbamate)(polymer);
(26) Zineb corresponding to the zinc salt of ethylenebis(dithiocarbamate)(polymer);
(27) Dichlofluanide corresponding to N-dichlorofluoromethylthio-N',N'-dimethyl-N-phenylsulfamide;
(28) Tolylfluanide corresponding to N-dichlorofluoromethylthio-N',N'-dimethyl-N-p-tolylsulfamide;
(29) Captano corresponding to N-(trichloromethylthio)cyclohex-4-ene-1,2-dicarboxyimide;
(30) Folpet corresponding to N-(trichloromethylthio)phthalimide;
(31) Dithianon corresponding to 5,10-dihydro-5,10-dioxonaphthol[2,3-b]-1,4-dithi-in-2,3-dicarbonitrile;
(32) Etridiazole corresponding to ethyl-3-trichloromethyl-1,2,4-thiadiazolyl ether;
(33) Hymexanol corresponding to 5-methylisoxazol-3-ole;
(34) Protiocarb corresponding to S-ethyl-(3-dimethylaminopropyl)thiocarbamate;
(35) Propamocarb corresponding to propyl-(3-dimethylaminopropyl)carbamate;
(36) A copper (I) salt or copper (II) salt, such as copper oxychloride, copper hydroxide, or copper sulfate;
(37) Mepanipyrim corresponding to N-(4-methyl-6-prop-1-inylpyrimidin-2-yl)aniline;
(38) Pirymethanil corresponding to N-(4,6-dimethylpyrimidin-2-yl)aniline;
(39) Cyprodinil corresponding to N-(4-methyl-6-cyclopropylpyrimidin-2-yl)aniline;
(40) R-3-aminobutanoic acid or RS-3-aminobutanoic acid.

The compounds having formula (I) can be obtained by means of numerous synthetic methods.

For merely illustrative but non-limiting purposes, schemes A and B indicate some preparations of compounds having formula (I) wherein $R_1$, $R_2$ and $R_3$ have the meanings already defined in the description of general formula (I).

Scheme A

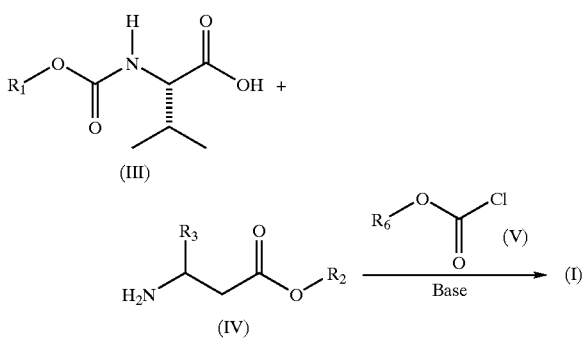

The carbamate (III) is reacted with an organic base, such as N-methylmorpholine, triethylamine, or N,N-dimethylbenzylamine, in an organic solvent such as dichloromethane, or ethyl acetate, or toluene, at a temperature ranging from −40° C. to 25° C. Alkyl chloroformiate (V) is then added, wherein $R_6$ has the meaning of a linear or branched $C_1$–$C_8$ alkyl group, such as for example, methyl, ethyl, isopropyl, isobutyl, the temperature being maintained within a range of −40° C. to 25° C. The ester (IV), optionally diluted in the reaction solvent, is then added, the temperature being maintained within a range of −40° C. to 30° C., obtaining the desired compound having formula (I).

Scheme B

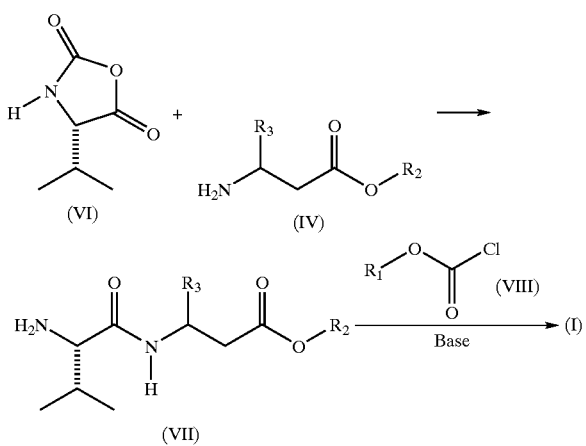

The ester (IV) is reacted with the anhydride (VI), whose preparation is described for example in "Berichte" (1906), Vol. 39, page 857 or in "Journal of Chemical Society" (1950), page 3213 and page 3461, in an organic solvent, such as dichloromethane, trichloromethane, ethyl acetate or tetrahydrofuran, in the presence of or without an organic base, such as triethylamine or N-methyl-N,N-dioctylamine, at a temperature ranging from −80° C. to room temperature, as described for example in "Journal of Chemical Society" (1950), page 3461. The dipeptide (VII) thus obtained is reacted, for example, in an organic solvent, such as dichloromethane or ethyl acetate, with the chloroformate (VIII) in the presence of an inorganic base, such as sodium bicabonate or potassium carbonate, or in the presence of an organic base, such as triethylamine, pyridine, N-methylmorpholine, N,N-dimethylbenzylamine, at a temperature ranging from −40° C. to 30° C., to obtain the desired compound having formula (I).

The carbamate (III) can be easily prepared by the addition of an alkylchloroformiate (VIII) to an aqueous solution of L-valine, in the presence of an inorganic base, such as sodium bicarbonate, potassium carbonate or sodium hydroxide, or an organic base such as triethylamine, at a temperature ranging from 0° C. to 25° C.; or by the addition of chloroformiate (VIII) to a solution of silanized L-valine, prepared "in situ" using the conditions described, for example, in "Berichte" (1967), Vol. 100, page 1638 or in "Berichte" (1970), Vol. 103, page 3353.

The racemic ester having formula (IV) can be obtained according to Scheme C below:

Scheme C

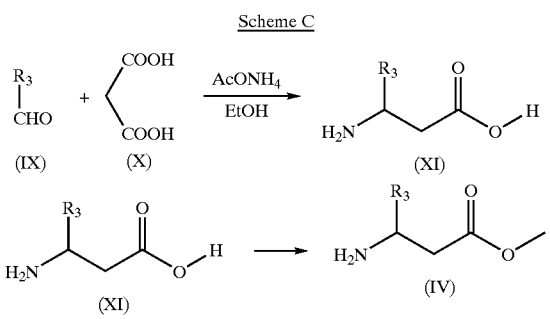

A suitable para-substituted benzaldehyde (IX) is reacted with malonic acid (X) in the presence of an ammonium salt, such as ammonium acetate or ammonium propionate, in a protic solvent, such as methyl alcohol, ethyl alcohol or ethylene glycol, at a temperature ranging from 40° C. to the boiling point of the pre-selected solvent, to obtain the desired β-amino acid (XI).

The β-amino acid (XI) thus obtained is transformed into methyl ester (VI) by means of one of the methods known in literature for the esterification of α-amino acids, for example, using solutions of a mineral acid, such as sulfuric acid or hydrochloric acid, or an organic acid, such as methanesulfonic acid or para-toluenesulfonic acid, in methanol, at a temperature ranging from room temperature to the boiling point of the solvent mixture; or by reacting said acid (XI) in methanol in the presence of equimolecular quantities or with an excess of thionyl chloride, at a temperature ranging from 20° C. to the boiling point of the solvent mixture.

In order to obtain compounds having formula (I) as a diastaereoisomeric mixture in which one of the diastereoisomeric forms is greater than 50%, an ester having formula (IV), in which one of the enantiomeric forms is greater than 50%, was obtained by the fractional crystallization of the salt formed by the reaction of the racemic ester (IV) with a suitable, optically active acid, such as tartaric acid, camphorsulfonic acid, O-(N-phenylaminocarbonyl)lactic acid, or an N-alkoxycarbonyl-α-amino acid.

Other methods for obtaining an ester having formula (IV) in an optically active form use an enantioselective, enzymatic hydrolysis of the racemic ester (IV) to obtain, depending on the enzyme used, the ester (IV) or acid (XI) in the desired enantiomeric form. The optically active acid (XI) is subsequently transformed into the required ester (IV) in the desired enantiomeric form, by one of the esterification methods already described for transforming the racemic acid (XI) into the racemic ester (IV).

Compound (I) is described in "The Pesticide Manual", 1983, VIIth edition, British Crop Protection Council Ed., page 148.

Compound (2) is described in "The Pesticide Manual", 1983, VIIth edition, British Crop Protection Council Ed., page 294.

Compound (3) is easily available on the market.

Compound (4) is described in "The Pesticide Manual", 1983, VIIth edition, British Crop Protection Council Ed., page 32.

Compound (5) is described in patent application WO 98 26654 A2.

Compound (6) is described in English patent GB 1,500,581.

Compound (7) is described in patent application WO 96 01559 A1.

Compound (8) is described in English patent GB 2,058,059.

Compound (9) is described in "Phytopatological News" (1978), Vol. 9, page 142.

Compound (10) is described in patent applications EP 610,764 and EP 550,788.

Compound (11) is described in European patent application EP 382,375.

Compound (12) is described in European patent application EP 253,213.

Compound (13) is described in American patent U.S. Pat. No. 5,185,242.

Compound (14) is described in American patent U.S. Pat. No. 4,931,581.

Compound (15) is described in "Brighton Crop Protection Conference—Pests and Diseases" (1996), Congress Acts.

Compound (16) is described in European patent application EP 629,616.

Compound (17) is described in European patent application EP 705,823.

Compound (18) is described in European patent application EP 31,257.

Compound (19) is described in European patent application EP 219,756.

Compound (20) is described in European patent applications EP 360,701 and EP 611,232.

Compound (21) is described in "The Pesticide Manual", 1983, VIIth edition, British Crop Protection Council Ed., page 120.

Compound (22) is described in "The Pesticide Manual", 1983, VIIth edition, British Crop Protection Council Ed., page 534.

Compound (23) is described in "The Pesticide Manual", 1983, VIIth edition, British Crop Protection Council Ed., page 469.

Compound (24) is described in "The Pesticide Manual", 1983, VIIth edition, British Crop Protection Council Ed., page 339.

Compound (25) is described in "The Pesticide Manual", 1983, VIIth edition, British Crop Protection Council Ed., page 340.

Compound (26) is described in "The Pesticide Manual", 1983, VIIth edition, British Crop Protection Council Ed., page 569.

Compound (27) is described in "The Pesticide Manual", 1983, VIIth edition, British Crop Protection Council Ed., page 175.

Compound (28) is described in "The Pesticide Manual", 1983, VIIth edition, British Crop Protection Council Ed., page 537.

Compound (29) is described in "The Pesticide Manual", 1983, VIIth edition, British Crop Protection Council Ed., page 87.

Compound (30) is described in "The Pesticide Manual", 1983, VIIth edition, British Crop Protection Council Ed., page 599.

Compound (31) is described in "The Pesticide Manual", 1983, VIIth edition, British Crop Protection Council Ed., page 225.

Compound (32) is described in "The Pesticide Manual", 1983, VIIth edition, British Crop Protection Council Ed., page 252.

Compound (33) is described in "The Pesticide Manual", 1983, VIIth edition, British Crop Protection Council Ed., page 314.

Compound (34) is described in "The Pesticide Manual", 1983, VIIth edition, British Crop Protection Council Ed., page 473.

Compound (35) is described in "The Pesticide Manual", 1983, VIIth edition, British Crop Protection Council Ed., page 471.

Compounds (36) are easily available on the market.

Compounds (37), (38) and (39) are described in "Pesticide Science" (1996), Vol. 47, pages 191–197.

Compound (40) is described in patent application WO 95 15684.

The fungicidal compositions comprising these compounds having formula (I) alone or mixed with one or more products (1)–(40), object of the present invention, have a high fungicidal activity with respect to numerous fungine species. Examples of pathogens controlled by the above compositions, and also examples of application crops, are provided hereunder for illustrative purposes only, without there being any limitations whatsoever:

*Plasmopara viticola* (vines);

*Phytophtora infestans* (tomatoes, potatoes);

*Phytophtora nicotianae* (tobacco, ornamental plants);

*Phytophtora paimivora* (cocoa);

*Phytophtora cinnamomi* (pineapples, citrus fruit);

*Phytophtora capsici* (peppers, tomatoes, cucurbitaceae);

*Phytophtora cryptogea* (tomatoes, plums, ornamental plants);

*Phytophtora megasperma* (ornamental plants);

*Phytophtora citri* (citrus fruit);

*Peronospora tabacina* (tobacco);

*Pseudoperonospora cubensis* (cabbages, cucurbitaceae);

*Pseudoperonospora humili* (hops);

Bremia (salad).

The compositions object of the present invention are capable of carrying out a high fungicidal action, allowing preventive, protective, prophylactive, systemic, curative and eradicative treatment to be applied.

The compositions object of the present invention can be used in different quantities depending on the crop, pathogen, environmental conditions and type of formulation adopted.

The application doses per hectare of compound having formula (I) are generally within the range of 5–500 g, whereas those of the possible compounds (1)–(40) present in the composition, are within the range of 5–3500 g.

The compositions object of the present invention can be applied to any part of the plant, for example leaves, stalks, branches and roots, or on the seeds themselves before sowing, or even on the ground where the plant grows.

The compositions object of the present invention are used in agronomic practice as compositions in various forms such as for example: dry powders, wettable powders, emulsifiable concentrates, micro-emulsions, pastes, granulates, solutions, suspensions, etc. The selection of the type of composition depends on the specific use.

The compositions are prepared with known methods, for example by diluting or dissolving the active substance with a solvent medium and/or a solid diluent, optionally in the presence of surface-active agents.

Solid diluents or carriers which can be used are: silica, kaolin, bentonite, talc, fossil flour, dolomite, calcium carbonate, magnesia, chalk, clays, synthetic silicates, attapulgite, sepiolite.

Various solvents, for example aromatics (xylols or mixtures of alkylbenzols), paraffins (petroleum fractions), alcohols (methanol, propanol, butanol, octanol, glycerine), amines, amides (N,N-dimethylformamide, N-methylpyrrolidone), ketones (cyclohexanone, acetone, acetophenone, isophorone, ethylamylketone), esters (isobutyl acetate, methyl esters of fatty acids obtained for example by the trans-esterification of vegetable oils), can be used as liquid diluents, in addition to water naturally.

Surface-active agents which can be used are salts of sodium, calcium, triethanolamine, or triethylamine of alkyl sulfonates, alkylarylsulfonates, polyethoxylated alkylphenols, fatty alcohols condensed with ethylene oxide, polyoxyethylated fatty acids, polyoxyethylated esters of sorbitol, ilgninsulfonates.

The compositions can also contain special additives for particular purposes such as, for example, adhesive agents, such as Arabic rubber, polyvinyl alcohol, polyvinylpyrrolidone.

The concentration of active substances in the above compositions varies from 0.1% to 98%, preferably from 0.5% to 90%.

If desired, it is possible to also add other compatible active principles to the compositions object of the present invention, such as for example, phytoregulators, antibiotics, herbicides, insecticides, fertilizers.

The following examples are provided for illustrative purposes and do not limit the scope of the present invention.

EXAMPLE 1

(a) Preparation of methyl (±)RS-[3-(N-isopropoxy-carbonyl-S-valinyl)amino]-3-(4-chlorophenyl)propanoate (epimeric form S—RS) (Compound Nr. 1)

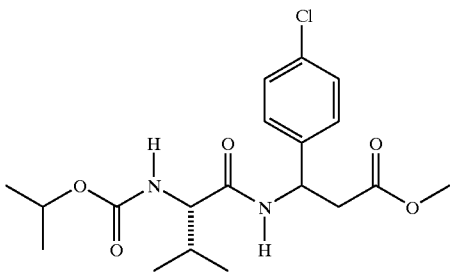

N-methylmorpholine (cm$^3$ 187) is added to a solution of N-isopropoxycarbonyl-S-valine (345 g) in trichloromethane (cm$^3$ 2300), cooled to −15÷−10° C., followed, after about 15' and at a temperature of −40÷−35° C., by a solution of isobutylchloroformiate (cm$^3$ 221) in trichloromethane (cm$^3$ 300). After about 30' and maintaining the same temperature, a solution of methyl RS-3-amino-3-(4-chlorophenyl) propanoate (360 g) in trichloromethane (cm$^3$ 600) is added dropwise. After letting the temperature rise to room values, the reaction is left under stirring for a night. Water (cm$^3$ 1400) is then added, which, after removing the organic phase, is extracted with trichloromethane (cm$^3$ 500×2 times). The organic phases are joined and washed with water (cm$^3$ 800×4), then dried on sodium sulfate and concentrated to a minimum volume at reduced pressure. The solution thus obtained is poured into a large volume of hexane maintained under vigorous stirring. The white crystal which is separated is collected by filtration, then washed with additional hexane, to obtain, after drying in air, 630 g of the desired product, for a yield of 94%.

The physico-chemical characterization of compound Nr. 1 gave the following results:

$[\alpha]_D^{25°\,C.}$ (C=1, CH$_2$Cl$_2$)=−12.5°

GC-MS: 398 (M$^+$), 212, 158, 116 (100%), 72

Elemental analysis [% found (theoretical)]=C, 52.4 (52.21); H, 6.80 (6.82); N, 7.05 (7.02); Cl, 8.85 (8.89).

b) Preparation of methyl (±)RS-3-amino-3-(4-chlorophenyl) propanoate

Thionyl chloride (304 g) is slowly added dropwise to a suspension of (±)RS-3-amino-3-(4-chlorophenyl)propanoic acid (507 g) in methanol (cm$^3$ 3000) maintained under vigorous stirring, the exothermy being controlled by means of the addition rate. The solution thus obtained is refluxed for about 8 hours and then concentrated to minimum volume. Water (cm$^3$ 1500) is added to the oil obtained, and is then extracted with ethyl ether (cm$^3$ 1000) and then basified with potassium carbonate until pH 8 is reached. The base aqueous solution thus obtained is extracted with ethyl acetate (cm$^3$ 700×3 times) and the organic phases are joined, dried on sodium sulfate and then evaporated at reduced pressure. The desired product is obtained (491 g) for a yield of 91%.

GC-MS: 213 (M$^+$), 198, 153, 140 (100%), 113, 77.

c) Preparation of (±)RS-3-amino-3-(4-chlorophenyl)-propanoic acid

A suspension of malonic acid (530 g), 4-chlorobenzaldehyde (666 g) and ammonium acetate (590 g) in ethanol (cm$^3$ 1500) is brought to reflux temperature under vigorous stirring for about 8 hours. The reaction mixture initially becomes limpid and then produces a constantly increasing precipitate. After cooling the whole mixture to room temperature, the crystal obtained is filtered (805 g) obtaining the desired product with a yield of 85%.

Elemental analysis [% found (theoretical)]=C, 54.01 (54.15); H, 5.10 (5.05); N, 7.12 (7.02); Cl, 17.80 (17.76).

EXAMPLE 2 a) Preparation of methyl (±)R-[3-(N-isopropoxycarbonyl-S-valinyl)amino]-3-(4-chlorophenyl)propanoate (diastereoisomeric form S—R) (Compound Nr. 2)

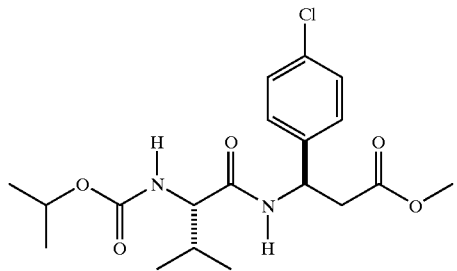

Compound Nr. 2 was obtained with a procedure and preparative scale analogous to that described in example 1, starting from an ester enriched in the enantiomeric form methyl R-3-amino-3-(4-chlorophenyl)propanoate (e.e. 80%, calculated by HPLC, using a chiral column) with an overall yield of 96%.

The physico-chemical characterization of compound Nr. 2 gave the following results:

Enantiomeric composition [S—R:S—S] (HPLC), chiral column=[80:20]

$[\alpha]_D^{25°\,C.}$ (C=1, CH$_2$Cl$_2$)=+4.4°

GC-IMS: 398 (M$^+$), 212, 158, 116 (100%), 72

Elemental analysis [% found (theoretical)]=C, 52.23 (52.21); H, 6.83 (6.82); N, 7.04 (7.02); Cl, 8.90 (8.89).

b) Preparation of methyl (+)R-3-amino-3-(4-chlorophenyl)propanoate

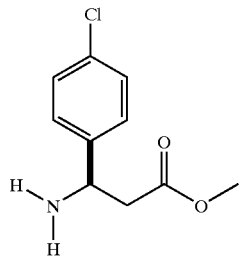

L-tartaric acid (35 g) is added to a solution of the ester methyl (±)RS-3-amino-3-(4-chlorophenyl)propanoate in methanol (cm³ 500). The solution which, under vigorous stirring, becomes limpid accompanied by a slight exothermy, is then brought to −10° C. The type of crystal is examined: in the case of the formation of vaporous crystals (racemic crystal) the solution is redissolved by diluting with additional methanol, until compact crystalline seeds are obtained on the bottom of the container.

After about 72 hours the precipitate is rapidly filtered, washed with ethyl ether and dried in air. The salt thus obtained (25 g) is dissolved in water to which potassium carbonate (26 g) is added and which is then extracted three times with dichloromethane. The organic phases joined and dried on sodium sulfate are evaporated at reduced pressure to obtain the desired product (15.2 g) for a yield of 60%.

$[\alpha]_D^{25°\ C.}$ (C=1, $CH_2Cl_2$)=+10°

Enantiomeric composition [S—R:S—S] (HPLC), chiral column=[80:20]

EXAMPLE 3 a) Preparation of methyl (−)S-[3-(N-isopropoxycarbonyl-S-valinyl)amino]-3-(4-chlorophenyl)propanoate (diastereoisomeric form S—S) (Compound Nr. 3)

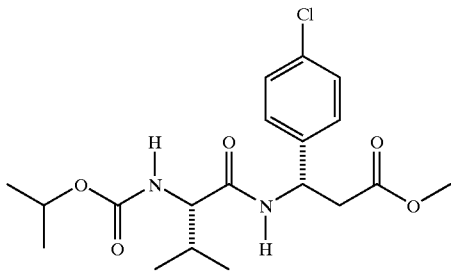

Compound Nr. 3 was obtained with a procedure and preparative scale analogous to that described in example 1, starting from an ester enriched in the enantiomeric form methyl S-3-amino-3-(4-chlorophenyl)propanoate (e.e. 90%, calculated by HPLC, using a chiral column) with an overall yield of 91%.

The physico-chemical characterization of compound Nr. 3 gave the following results:

Enantiomeric composition [S—R:S—S] (HPLC), chiral column=[10:90]

$[\alpha]_D^{25°\ C.}$ (C=1, $CH_2Cl_2$)=−24.4°

GC-MS: 398 (M⁺), 212, 158, 116 (100%), 72

Elemental analysis [% found (theoretical)]=C, 52.21 (52.21); H, 6.81 (6.82); N, 6.99 (7.02); Cl, 8.88 (8.89).

b) Preparation of methyl (−)S-3-amino-3-(4-chlorophenyl)propanoate

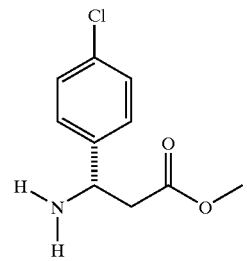

Compound Nr. 3 was obtained with a procedure and preparative scale analogous to that described in example 2 for the preparation of the ester methyl R-3-amino-3-(4-chlorophenyl)propanoate, but using D-tartaric acid as resolvent agent, with a yield of 48%.

Enantiomeric composition [S—R:S—S] (HPLC), chiral column=[10:90]

$[\alpha]_D^{25°\ C.}$ (C=1, $CH_2Cl_2$)=−9.6°

EXAMPLE 4

Using preparative procedures analogous to those described in the previous examples, the following compounds indicated together with their chemical characterization, were prepared:

methyl RS-[3-(N-isopropoxycarbonyl-S-valinyl)amino]-3-(4-methylphenyl)propanoate (epimeric form S—RS) (Compound Nr. 4)

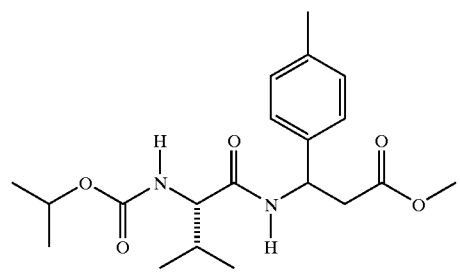

$[\alpha]_D^{25°\ C.}$ (C 1, $CH_2Cl_2$)=−10.7°

Elemental analysis [% found (theoretical)]=C, 63.42 (63.47); H, 7.89 (7.99); N, 7.33 (7.40).

methyl RS-[3-(N-phenoxycarbonyl-S-valinyl)amino]-3-(4-ethylphenyl)propanoate (epimeric form S—RS) (Compound Nr. 5)

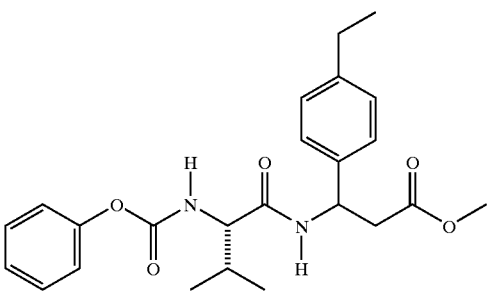

Elemental analysis [% found (theoretical)]=C, 67.49 (67.59); H, 6.99 (7.09); N, 6.59 (6.57).

methyl RS-[3-(N-isopropoxycarbonyl-S-valinyl)amino]-3-(4-methoxyphenyl)propanoate (epimeric form S—RS) (Compound Nr. 6)

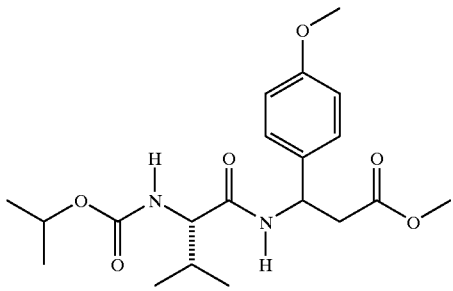

Elemental analysis [% found (theoretical)]=C, 60.96 (60.90); H, 7.22 (7.67); N, 7.23 (7.10).

methyl RS-[3-(N-isopropoxycarbonyl-S-valinyl)amino]-3-(4-cyanophenyl)propanoate (epimeric form S—RS) (Compound Nr. 7)

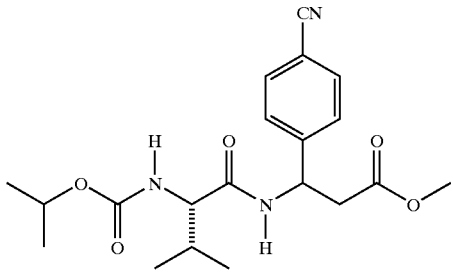

$[\alpha]_D^{25°\ C.}$ (C=1, CH$_2$Cl$_2$)=−11.9°

Elemental analysis [% found (theoretical)]=C, 61.70 (61.68); H, 7.02 (6.99); N, 10.72 (10.79).

EXAMPLE 5 a) Preparation of methyl (±)RS-[3-(N-isopropoxycarbonyl-S-valinyl)amino]-3-(benzothiazol-2-yl)propanoate (epimeric form S—RS) (Compound Nr. 8)

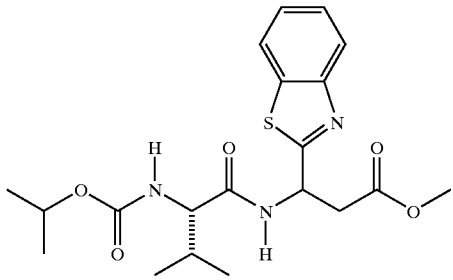

Compound Nr. 8 was obtained with a procedure and preparative scale analogous to that described in example 1, starting from an ester methyl RS-3-amino-3-(benzothiazol-2-yl)propanoate with an overall yield of 74%.

The physico-chemical characterization of compound Nr. 8 gave the following results:

Elemental analysis [% found (theoretical)]=C, 56.91 (56.99); H, 6.42 (6.46); N, 10.03 (9.97); S, 7.55 (7.61).

b) Preparation of methyl (±)RS-3-amino-3-(benzothiazol-2-yl)propanoate

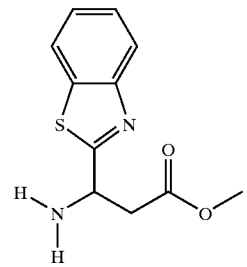

Methyl γ-ester hydrochloride of aspartic acid (500 g) and phosphorous oxychloride (cm$^3$ 250) are added, in order, to a solution of 2-aminothiophenol (337 g) in toluene (cm$^3$ 2500). The reaction is refluxed for about 20', with the formation of rubbery masses. The liquid phase is decanted, an aqueous solution of sodium hydroxide is added and the solution thus obtained is extracted with ethyl acetate. The organic phase is evaporated at reduced pressure and the oil obtained is crystallized with ethyl ether. An impure yellow solid is obtained, which is used directly for the previous reaction without any further purification.

GC-MS: 236(M$^+$), 163 (100%), 136, 102, 70

EXAMPLE 6 a) Preparation of methyl (±)RS-[3-(N-isopropoxycarbonyl-S-valinyl)amino]-3-(5-chlorobenzothiazol-2-yl)propanoate (epimeric form S—RS) (Compound Nr. 9)

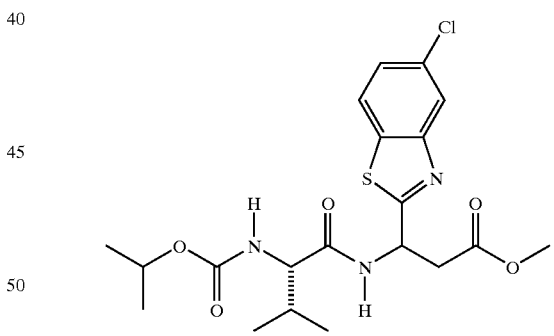

Compound Nr. 9 was obtained with a procedure and preparative scale analogous to that described in example 1, starting from the ester methyl RS-3-amino-3-(5-chlorobenzo-thiazol-2-yl)propanoate with an overall yield of 68%.

The physico-chemical characterization of compound Nr. 9 gave the following results:

Elemental analysis [% found (theoretical)]=C, 52.73 (52.68); H, 5.72 (5.75); N, 9.12 (9.22); Cl, 7.72 (7.78); S, 6.97 (7.03).

b) Preparation of methyl (±)RS-3-amino-3-(5-chlorobenzothiazol-2-yl)propanoate

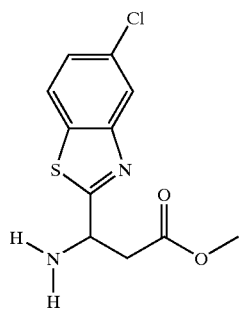

The ester methyl RS-3-amino-3-(5-chlorobenzothiazol-2-yl)propanoate was obtained with a procedure analogous to that described in example 5 for the ester methyl RS-3-amino-3-(benzothiazol-2-yl)propanoate.

GC-MS: 270(M$^+$), 211, 197(100%), 170, 102, 70

EXAMPLE 6

Determination of the Fungicidal Effectiveness Against Peronospora (*Plasmapara viticola*) of Compounds Having Formula (I) and (II) in Preventive Leaf Application Cultivar Dolcetto vine leaves, grown in vases in a conditioned environment (20±1° C.), 70% relative humidity), are treated by spraying both sides of the leaves with compounds 1–7 dispersed in a hydroacetone solution at 20% by volume of acetone.

After remaining 24 hours in a conditioned environment, the plants are sprayed on both sides of the leaf with an aqueous suspension of conidia of *Plasmopara viticola* (200,000 conidia per cm$^3$).

The plants are kept in a humidity saturated environment, at 21° C., for the incubation period of the fungus and, at the end of this period (7 days), the fungicidal activity is evaluated according to an evaluation percentage scale from 100 (healthy plant) to 0 (completely infected plant).

The data obtained with compounds 1–8 and with the reference compounds are indicated in Table 1 below.

TABLE 1

| Antiperonosporic effectiveness in preventive leaf appplication on vines | Effectiveness expressed as leaf diffusion control % of the disease with respect to a non-treated reference and with the following doses: Dose (g/hl) | | | |
|---|---|---|---|---|
| Compound | 30 | 7.5 | 1.8 | 0.45 |
| 1 | 100 | 100 | 100 | 80 |
| 2 | 100 | 100 | 100 | 100 |
| 3 | 100 | 100 | 85 | 65 |
| 4 | 100 | 100 | 100 | 75 |
| 5 | 100 | 100 | 90 | 70 |
| 6 | 100 | 100 | 92 | 65 |
| 7 | 100 | 10& | 90 | 67 |
| 8 | 100 | 100 | 92 | 70 |
| 9 | 100 | 100 | 100 | 90 |
| Reference 1 | 100 | 90 | 20 | 0 |
| Reference 2 | 100 | 88 | 65 | 30 |
| Reference 3 | 100 | 91 | 55 | 10 |
| Reference 4 | 90 | 75 | 55 | 15 |
| Reference 5 | 96 | 75 | 15 | 0 |

List of references indicated in Tables 1a–b

Reference 1 (EP 0 718 280 A2, compound Nr. 4.4):

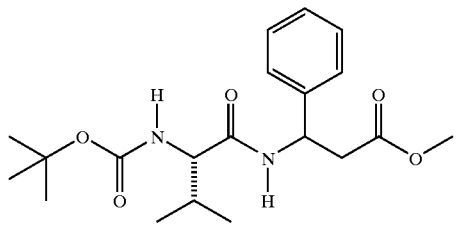

Reference 2 (EP 0 718 280 A2, compound Nr. 4.10):

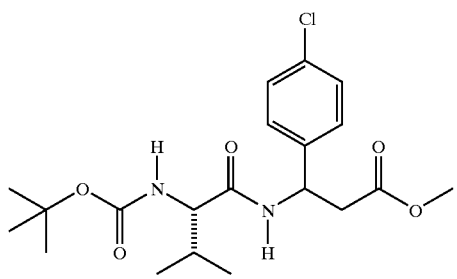

Reference 3 (EP 0 718 280 A2, compound Nr. 16.6):

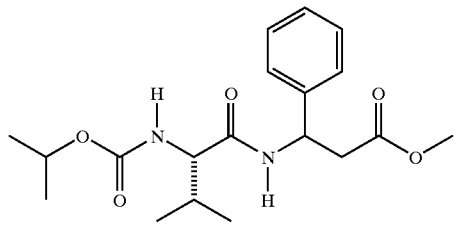

Reference 4 (EP 0 718 280 A2, compound Nr. 16.9):

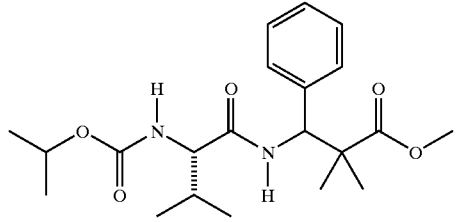

Reference 5 (EP 0 652 229 A2, compound Nr. 58):

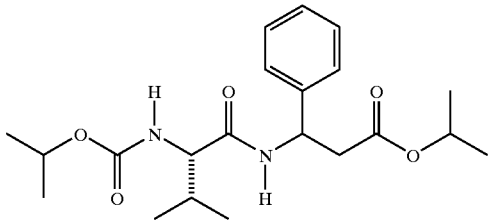

What is claimed is:

1. A dipeptide compound having the general formula (I):

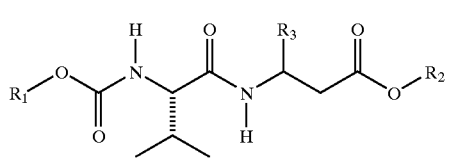

(I)

wherein:
- R₁ represents an isopropyl or phenyl group;
- R₂ represents a methyl group;
- R₃ is a phenyl group substituted in position 4 with an R₄ group; a 2-benzothiazole group; or a 2-benzothiazole group substituted with an R₅ group;
- R₄ and R₅ are each independently selected from the group consisting of a fluorine atom, a chlorine atom, a methyl group, an ethyl group, a methoxyl group, and a cyano group;

or a stereoisomer or a mixture of stereoisomers thereof.

2. The compound of claim 1, wherein R₁ is isopropyl.

3. The compound of claim 1, wherein R₁ is phenyl.

4. The compound of claim 1, wherein R₃ is a phenyl group substituted in position 4 with an R₄ group.

5. The compound of claim 1, wherein R₃ is a 2-benzothiazole group.

6. The compound of claim 1, wherein R₃ is a 2-benzothiazole group substituted with an R₅ group.

7. The compound of claim 1, wherein the chiral center of the aromatic β-amino acid residue of formula (I) is R.

8. The compound of claim 1, wherein the chiral center of the aromatic β-amino acid residue of formula (I) is S.

9. A dipeptide compound having general formula (I) wherein the absolute configuration of the chiral atom of the valine residue in formula (I) is S and that of the aromatic β-amino acid residue in formula (I) is R, as represented by general formula (II):

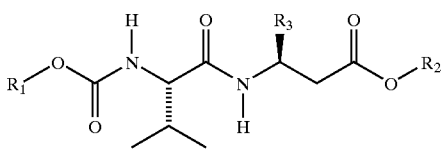

(II)

wherein:
R₁, R₂, and R₃ have the meanings defined in claim 1.

10. A mixture comprising a compound according to claim 1 and at least one stereoisomer thereof.

11. The mixture of stereoisomers according to claim 1, consisting of methyl R-[3-(N-isopropoxycarbonyl-S-valinyl)amino]-3-(4-chlorophenyl)propanoate and methyl S-[3-(N-isopropoxycarbonyl-S-valinyl)amino]-3-(4-chlorophenyl)propanoate.

12. The compound according to claim 1, consisting of methyl R-[3-(N-isopropoxycarbonyl-S-valinyl)amino]-3-(4-chlorophenyl)propanoate.

13. The compound according to claim 1, consisting of methyl S-[3-(N-isopropoxycarbonyl-S-valinyl)amino]-3-(4-chlorophenyl)propanoate.

14. The mixture of stereoisomers according to claim 1, consisting of methyl R-[3-(N-isopropoxycarbonyl-S-valinyl)amino]-3-(4-methylphenyl)propanoate and methyl S-[3-(N-isopropoxycarbonyl-S-valinyl)amino]-3-(4-methylphenyl)propanoate.

15. The mixture of stereoisomers according to claim 1, consisting of methyl R-[3-(N-phenoxycarbonyl-S-valinyl)amino]-3-(4-ethylphenyl)propanoate and methyl S-[3-(N-phenoxycarbonyl-S-valinyl)amino]-3-(4-ethylphenyl)propanoate.

16. The mixture of stereoisomers according to claim 1, consisting of methyl R-[3-(N-isopropoxycarbonyl-S-valinyl)amino]-3-(4-methoxyphenyl)propanoate and methyl S-[3-(N-isopropoxycarbonyl-S-valinyl)amino]-3-(4-methoxyphenyl)propanoate.

17. The mixture of stereoisomers according to claim 1, consisting of methyl R-[3-(N-isopropoxycarbonyl-S-valinyl)amino]-3-(4-cyanophenyl)propanoate and methyl S-[3-(N-isopropoxycarbonyl-S-valinyl)amino]-3-(4-cyanophenyl)propanoate.

18. The mixture of stereoisomers according to claim 1, consisting of methyl R-[3-(N-isopropoxycarbonyl-S-valinyl)amino]-3-(benzothiazol-2-yl)propanoate and methyl S-[3-(N-isopropoxycarbonyl-S-valinyl)amino]-3-(benzothiazol-2-yl)propanoate.

19. The mixture of stereoisomers according to claim 1, consisting of methyl R-[3-(N-isopropoxycarbonyl-S-valinyl)amino]-3-(5-chlorobenzothiazol-2-yl)propanoate and methyl S-[3-(N-isopropoxycarbonyl-S-valinyl)amino]-3-(5-chlorobenzothiazol-2-yl)propanoate.

20. A process for the preparation of a fungicidal composition comprising:
(a) dissolving or mixing the compound of claim 1 in a liquid medium or
(b) diluting or mixing the compound of claim 1 with a solid diluent or carrier,
for a time and under conditions suitable for the formation of a fungicidal composition, and
(c) recovering the fungicidal composition of step (a) or (b).

21. The process of claim 20, wherein step (a) or (b) is performed in the presence of a surface-active agent.

22. A process for the preparation of a compound having formula (I):

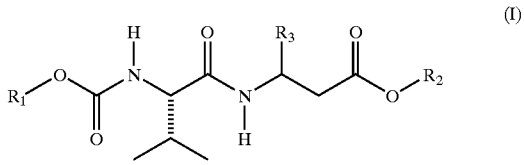

(I)

comprising the following reaction scheme:

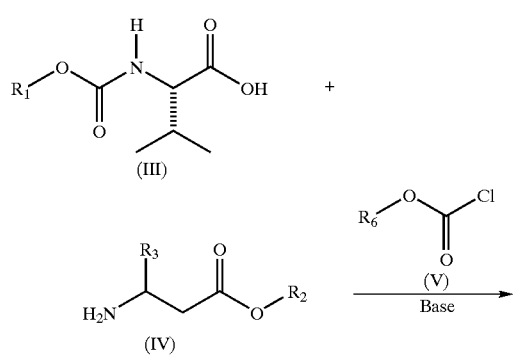

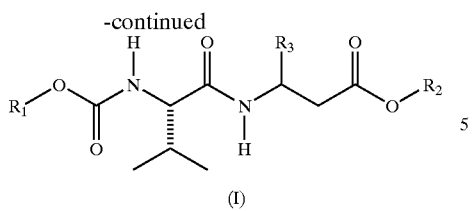

(I)

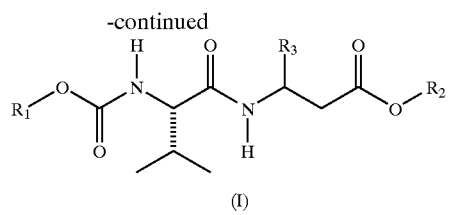

(I)

wherein:

$R_1$, $R_2$ and $R_3$ have the meanings defined in claim 1, and $R_6$ is a linear or branched $C_1$–$C_8$ alkyl group; and wherein said reaction scheme is characterized by:

(a) combining the carbamate (III) with an organic base in an organic solvent, while maintaining the temperature within the range of −40° C. to 25° C.;

(b) reacting the alkyl chloroformate (V) with the carbamate of formula (III) at a temperature within the range of −40° C. to 25° C. for a time and under conditions effective to form a reaction product;

(c) reacting the β-amino ester of formula (IV), with the reaction product of step (b) at a temperature within the range of −40° C. to 30° C. for a time and under conditions effective to form a compound of formula (I); and (d) recovering or isolating a compound of formula (I).

23. A process for the preparation of a compound having formula (I):

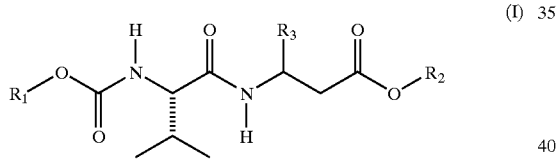

(I)

comprising the following reaction scheme:

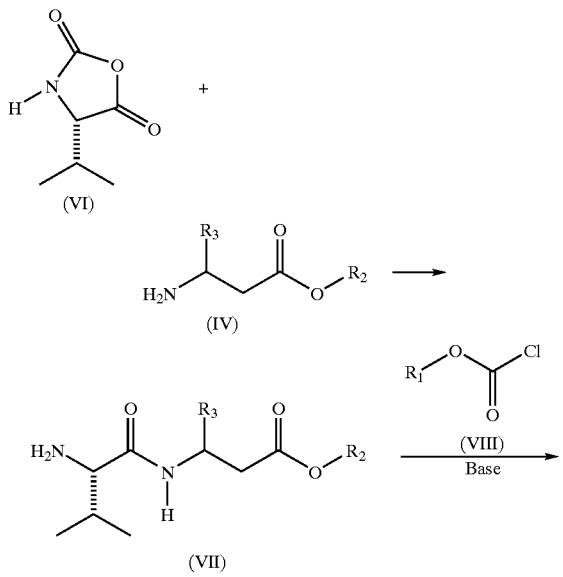

wherein:

$R_1$, $R_2$ and $R_3$ have the meanings defined in claim 1, and wherein said reaction scheme is characterized by:

(a) reacting ester (IV) with anhydride (VI) in an organic solvent, optionally in the presence of an organic base, at a temperature within the range of −80° C. to room temperature for a time and under conditions effective to form a dipeptide of formula VII;

(b) reacting the dipeptide (VII) thus obtained, in an organic solvent, with chloroformate (VIII) in the presence of an inorganic base or an organic base, at a temperature within the range of −40° C. to 30° C., for a time and under conditions effective to form a compound of formula I; and (c) isolating or recovering a compound of formula (I).

24. The process according to claim 22 or 23, wherein the ester of formula IV is enriched in either the R or S enantiomer.

25. The process according to claim 24, wherein the ester of formula IV is obtained by:

(a) treating a mixture of R and S enantiomers of formula (IV) with an optically active acid to form a mixture of salts of the R and S enantiomers;

(b) fractionally crystallizing the salts of the enantiomers to obtain a salt of a compound of formula IV which is enriched in either the R or the S enantiomer;

(c) converting the salt of step (b) which is enriched in either the R or the S enantiomer into an ester of formula (IV); and (d) isolating or recovering the ester of step (c).

26. The process according to claim 24, wherein the ester of formula IV is obtained by:

i) reacting a mixture of D- and L-stereoisomers of formula IV with a hydrolytic enzyme for a time and under conditions effective to preferentially hydrolyze either the D- or L-stereoisomer to the corresponding carboxylic acid, and ii) isolating the stereoisomer that is not hydrolyzed by the enzyme.

27. The process according to claim 24, wherein the ester of formula IV is obtained by:

i) reacting a mixture of D- and L-stereoisomers of formula IV with a hydrolytic enzyme for a time and under conditions effective to preferentially hydrolyze either the D- or the L-stereoisomer to the corresponding carboxylic acid;

ii) separating the carboxylic acid of step (i) from the unhydrolyzed ester of formula IV;

iii) reacting the carboxylic acid of step (ii) with methanol for a time and under conditions effective to form an ester of formula IV; and iv) isolating the ester of formula IV.

28. A fungicidal composition comprising:

(a) a compound according to claim 1, (b) a solid carrier or liquid diluent, and (c) a fungicide selected from the group consisting of:
(1) Cymoxanil or 1-(2-cyano-2-methoxyimino-acetyl)-3-ethylurea;
(2) Fosetyl-Al or the aluminum salt of ethyl hydrogen phosphonate;
(3) Potassium phosphonate;
(4) Benalaxyl or methyl N-(phenylacetyl)-N-2,6-xylyl-R, S-alaninate;
(5) Methyl N-(phenylacetyl)-N-2,6-xylyl-R-alaninate;
(6) Metalaxyl or methyl N-(2-methoxyacetyl-N-2,6-xylyl-R,S-alaninate;
(7) Mefenoxam or methyl N-(2-methoxyacetyl-N-2,6-xylyl-R-alaninate;
(8) Oxadixyl or 2-methoxy-N-(2-oxo-1,3 oxazolidin-3-yl) acet-2',6'-xylidinide;
(9) Ofurace or D, L-3-[N-chloroacetyl-N-(2,6-xylyl)-amino]-γ-butyrolactone;
(10) Iprovalicarb or O-(1-methylethyl)N-[2-methyl-1-[[[1-(4-methylphenyl)ethyl]-amino]carbonyl]propyl] carbamate;
(11) Azoxystrobin or methyl (E)-2-[2-[6(2-cyanophenoxy)-pyrimidin-4-yloxy]phenyl]-3-methoxyacrylate;
(12) Kresoxym-methyl or methyl (E)-methoxyimino-α-[o-tolyloxy)-o-tolyl]acetate;
(13) Metominofen or the experimental abbreviation SSF-126 or N-methyl(E)-methoxyimino-(2-phenoxyphenyl)acetamide;
(14) Acylbenzolar or methylbenzothiadiazole-7-thiocarboxylate;
(15) Famoxadone or 5-methyl-5-(4-phenoxyphenyl)-3-(phenylamino)oxazolidin-2,4-dione;
(16) Fenamidone or 4-methyl-4-phenyl-1-(phenylamino)-2-methylthioimidazolidin-5-one;
(17) IKF916 or 2-cyano-4-chloro-5-(4-methylphenyl)-1-(N,N-dimethylaminosulfamoyl)imidazole;
(18) Fluazinam or 3-chloro-N-(3-chloro-5-trifluoromethyl-2 -pyridyl)-α,α,α-trifluoro-2,6-dinitro p-toluidine;
(19) Dimethomorph or (E,Z)-4-[3-(4-chlorophenyl)-3-(3, 4-dimethoxyphenyl)acryloyl]morpholine;
(20) Flumetover or N,N-diethylamide of 4-trifluoromethyl-6-(3,4-dimethoxyphenyl)benzoic acid;
(21) Chlorothalonil or 1,3-dicyano-2,4,5,6-tetrachlorobenzene;
(22) Thiram or bis-(dimethylthiocarbamoyl)disulfide (polymer);
(23) Propineb or the zinc salt of propylenebis (dithiocarbamate) (polymer);
(24) Mancozeb or the manganese and zinc salt of ethylenebis(dithiocarbamate)(polymer);
(25) Maneb or the manganese salt of ethylenebis (dithiocarbamate)(polymer);
(26) Zineb or the zinc salt of ethylenebis(dithiocarbamate) (polymer);
(27) Dichlofluanide or N-dichlorofluoromethylthio-N',N'-dimethyl-N-phenylsulfamide;
(28) Tolylfluanide or N-dichlorofluoromethylthio-N',N'-dimethyl-N-p-tolylsulfamide;
(29) Captano or N-(trichloromethylthio)cyclohex-4-ene-1,2-dicarboxyimide;
(30) Folpet or N-(trichloromethylthio)phthalimide;
(31) Dithianone or 5,10-dihydro-5,10dioxonaphthol[2,3-b]-1,4-dithi-in-2,3-dicarbonitrile;
(32) Etridiazole or ethyl-3-trichloromethyl-1,2,4-thiadiazolyl ether;
(33) Hymexanol or 5-methylisoxazol-3-ole;
(34) Protiocarb or S-ethyl-(3-dimethylaminopropyl) thiocarbamate;
(35) Propamocarb or propyl-(3-dimethylaminopropyl) carbamate;
(36) A cuprous (copper (I)) salt or cupric (copper (II)) salt;
(37) Mepanipyrim or N-(4-methyl-6-prop-1-inylpyrimidin-2-yl)aniline;
(38) Pirymethanil or N-(4,6-dimethylpyrimidin-2-yl) aniline;
(39) Cyprodinil or N-(4-methyl -6-cyclopropylpyrimidin-2-yl)aniline; and
(40) R-3-aminobutanoic acid or R, S-3-aminobutano acid.

29. A fungicidal composition comprising:
(a) a compound according to claim 1;
(b) an agent selected from the group consisting of a phytoregulator, an antibiotic, a herbicide and an insecticide; and
(c) a solid carrier or a liquid diluent.

30. A fungicidal composition comprising a compound according to claim 1, and a fertilizer.

31. A fungicidal composition comprising the compound of claim 1 and a liquid diluent selected from the group consisting of an aromatic solvent, paraffin, an alcohol, an amine, an amide, a ketone, an ester, and water.

32. A fungicidal composition comprising the compound of claim 1 and a surface active agent.

33. A fungicidal composition comprising a compound according to claim 1, together with a solid carrier or a liquid diluent.

34. The composition according to claim 33, wherein the concentration of the compound having formula (I) ranges from 0.5 to 90% by volume.

35. The composition of claim 33, in the form of a dry powder, wettable powder, emulsifiable concentrate, microemulsion, paste, granulate, solution or suspension.

36. A fungicidal composition comprising:
(a) a compound according to claim 1,
(b) a compound or material selected from the group consisting of a surface-active agent, an adhesive agent, polyvinyl alcohol and polyvinylpyrrolidone, and
(c) a solid carrier or a liquid diluent.

37. The fungicidal composition according to claim 36 that comprises an adhesive agent which is Arabic rubber.

38. A fungicidal composition comprising the compound of claim 1 and a solid diluent or carrier selected from the group consisting of silica, kaolin, bentonite, talc, fossil flour, dolomite, calcium carbonate, magnesia, chalk, clay, synthetic silicate, attapulgite and sepiolite.

39. A method for inhibiting fungal growth on the roots of a plant, comprising applying a fungicidal composition according to claim 33 to the hypogeous surfaces of the plant, for a time and under conditions effective to inhibit said fungal growth.

40. A method for inhibiting the growth of a fungus in a plant, comprising applying a composition according to claim 33 to a plant, a seed, or to the soil in the vicinity of a plant, for a time and under conditions effective to inhibit growth of a fungus.

41. The method according to claim 40, wherein the fungicidal composition is applied to all surfaces of the plant.

42. The method according to claim 40, wherein the fungicidal composition is applied to the leaves, stems, shoots or branches of the plant.

43. The method according to claim 19, wherein the fungicidal composition is applied to the soil in the vicinity of the plant.

44. The method according to claim 43, wherein the fungicidal composition is applied to the seeds prior to sowing.

45. A method for inhibiting the growth of a fungus in a plant comprising applying a composition according to claim 28 to a plant, or to the soil in the vicinity of a plant, for a time and under conditions effective to inhibit the growth of a fungus.

46. The method according to claim 45 wherein said compound of formula I is applied at a dose of 5–500 grams per hectare, and said fungicide is applied at a dose of 5–3500 grams per hectare.

47. A method of inhibiting the growth of a fungus comprising: contacting said fungus with a dipeptide compound having formula (1):

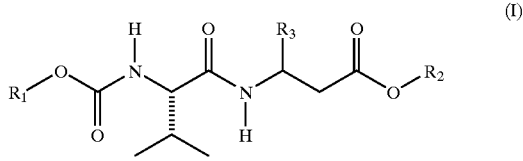

for a time and under conditions effective to inhibit growth of said fungus, wherein $R_1$ is an isopropyl or phenyl group;

$R_2$ is a methyl group;

$R_3$ is selected from the group consisting of a phenyl group substituted in the para position with $R_4$, a 2-benzothiazole group, and a 2-benzothiazole group substituted with $R_5$;

$R_4$ and $R_5$ are each independently selected from the group consisting of a fluorine atom, a chlorine atom, a methyl group, an ethyl group, a methoxy group, and a cyano group;

or a stereoisomer thereof or a mixture of stereoisomers thereof.

* * * * *